(12) United States Patent
Hessler et al.

(10) Patent No.: US 12,016,786 B2
(45) Date of Patent: Jun. 25, 2024

(54) POSITIONING AND ADJUSTING TWO AXIS JOINT IMPLANTS

(71) Applicant: GLOBUS MEDICAL, INC., Audubon, PA (US)

(72) Inventors: Tyler Hessler, Phoenixville, PA (US); Jenna Israel, Eagleville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 18/352,606

(22) Filed: Jul. 14, 2023

(65) Prior Publication Data

US 2023/0355410 A1 Nov. 9, 2023

Related U.S. Application Data

(63) Continuation of application No. 17/529,371, filed on Nov. 18, 2021, now Pat. No. 11,730,609, which is a continuation of application No. 16/558,364, filed on Sep. 3, 2019, now Pat. No. 11,197,767.

(51) Int. Cl.
| | |
|---|---|
| *A61F 2/46* | (2006.01) |
| *A61F 2/44* | (2006.01) |
| *A61F 2/30* | (2006.01) |

(52) U.S. Cl.
CPC ............ *A61F 2/4611* (2013.01); *A61F 2/447* (2013.01); *A61F 2002/3054* (2013.01); *A61F 2/4603* (2013.01); *A61F 2002/4627* (2013.01); *A61F 2002/4629* (2013.01)

(58) Field of Classification Search
CPC ...... A61F 2/4611; A61F 2/447; A61F 2/4603; A61F 2002/3054; A61F 2002/4627; A61F 2002/4629

USPC ...................... 606/99, 279; 623/17.11–17.16
See application file for complete search history.

(56) References Cited

U.S. PATENT DOCUMENTS

| | | | | |
|---|---|---|---|---|
| 10,159,583 | B2 * | 12/2018 | Dietzel | A61F 2/4657 |
| 2007/0123905 | A1 * | 5/2007 | Schneid | A61F 2/4425 |
| | | | | 606/99 |
| 2010/0100100 | A1 * | 4/2010 | Refai | A61F 2/4611 |
| | | | | 606/99 |
| 2013/0053966 | A1 * | 2/2013 | Jimenez | A61F 2/4425 |
| | | | | 623/17.16 |
| 2017/0246000 | A1 * | 8/2017 | Pavlov | A61B 17/7055 |
| 2018/0000606 | A1 * | 1/2018 | Hessler | A61F 2/447 |

FOREIGN PATENT DOCUMENTS

JP 2012505714 A 3/2012

* cited by examiner

*Primary Examiner* — Jessica Weiss

(57) ABSTRACT

An inserter connects to an implant which has two rotatable actuators for adjusting two different parameters of the insert. The inserter has a handle and a frame extending from the handle. A hollow tube is supported by the frame and has an end that can be connected and disconnected from the implant when the tube is rotated. A stem is passed through the tube, and another stem is supported by the frame. Each of the stems has an end that is connectable to an actuator of the implant, and an opposite end connectable to a tool driver. When the tool driver rotates a stem connected to the implant, a parameter of the implant is changed. The stems can be removed for cleaning or for replacement with a different type of stem. The two parameters can be a height of different sides of the implant.

18 Claims, 5 Drawing Sheets

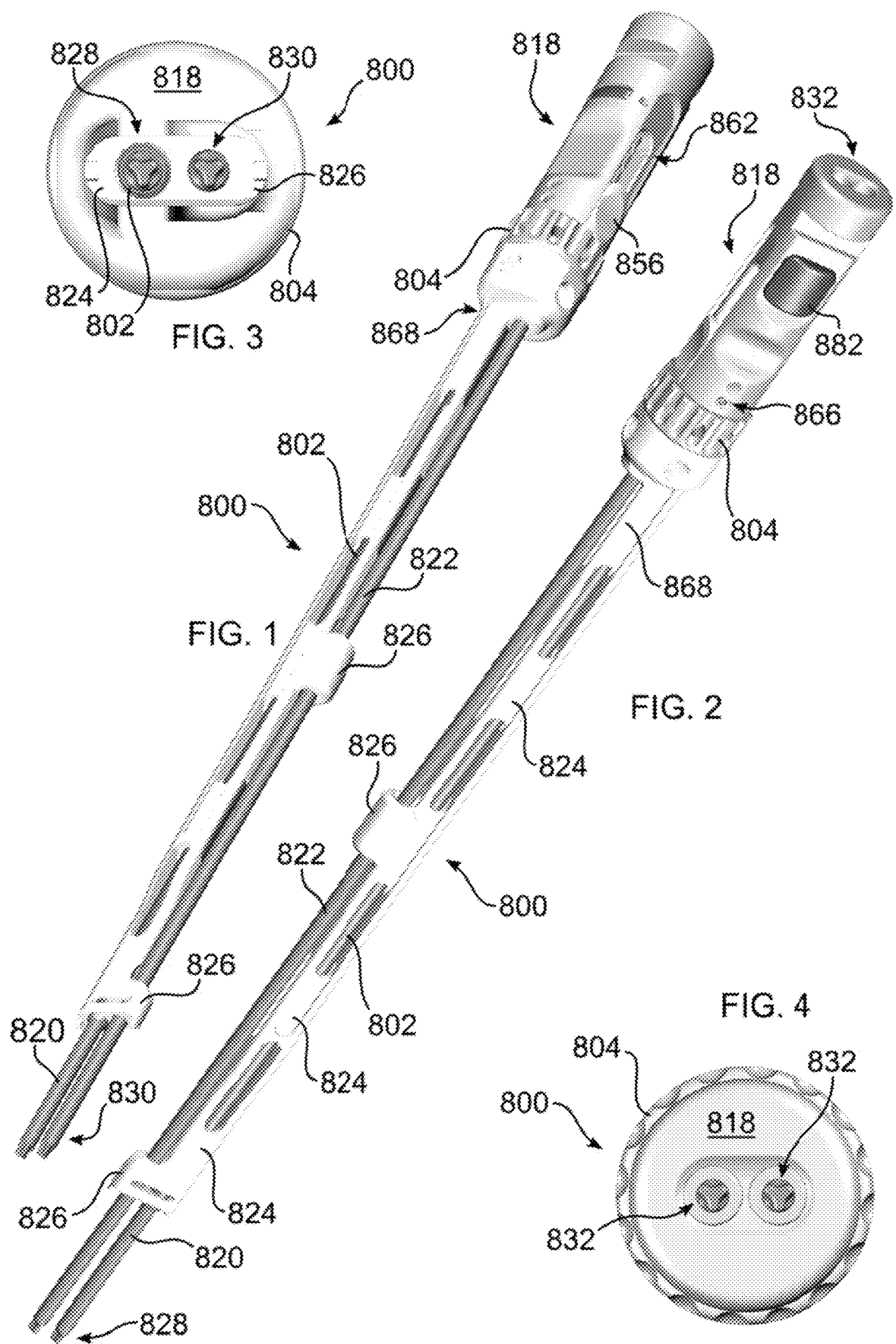

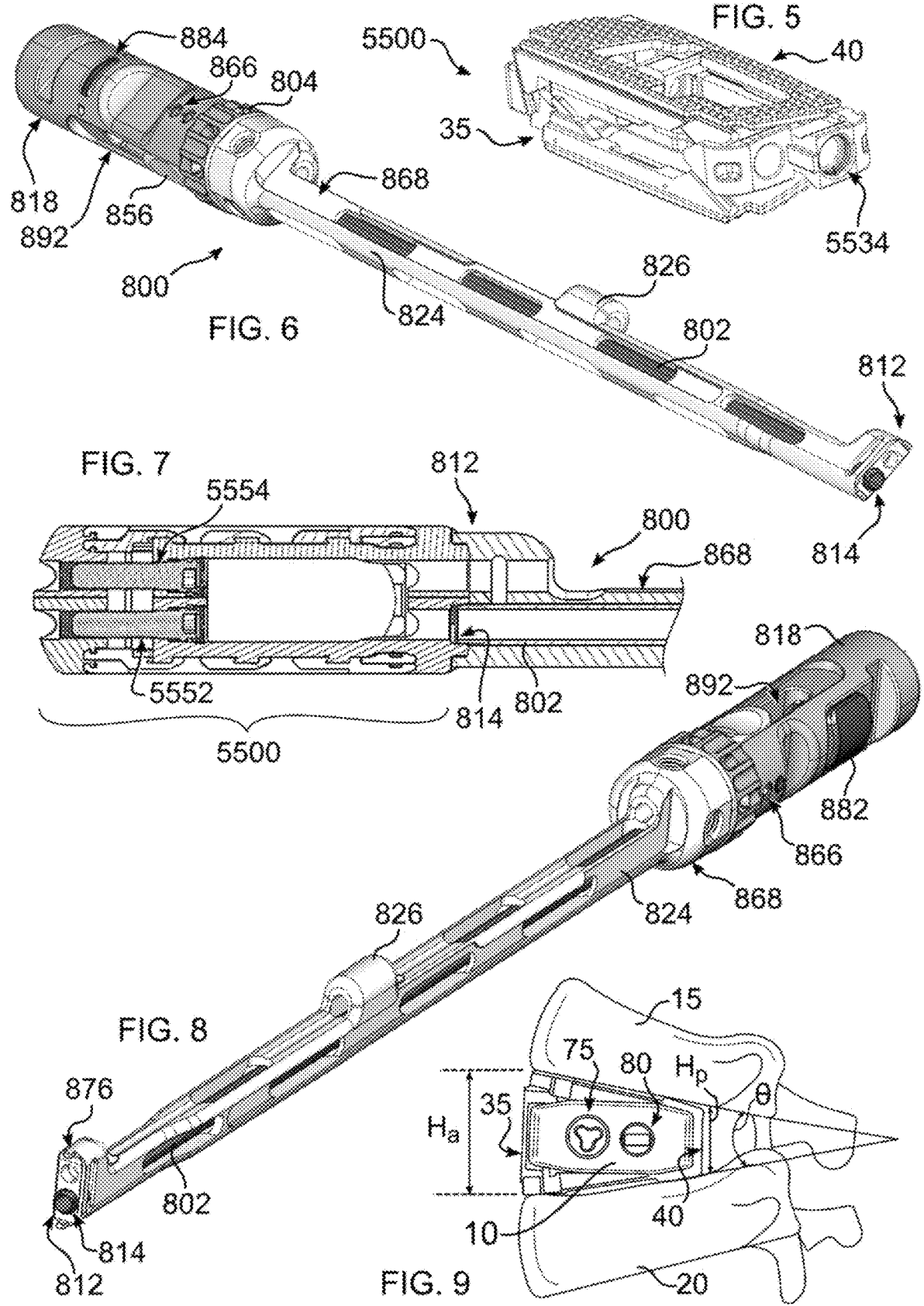

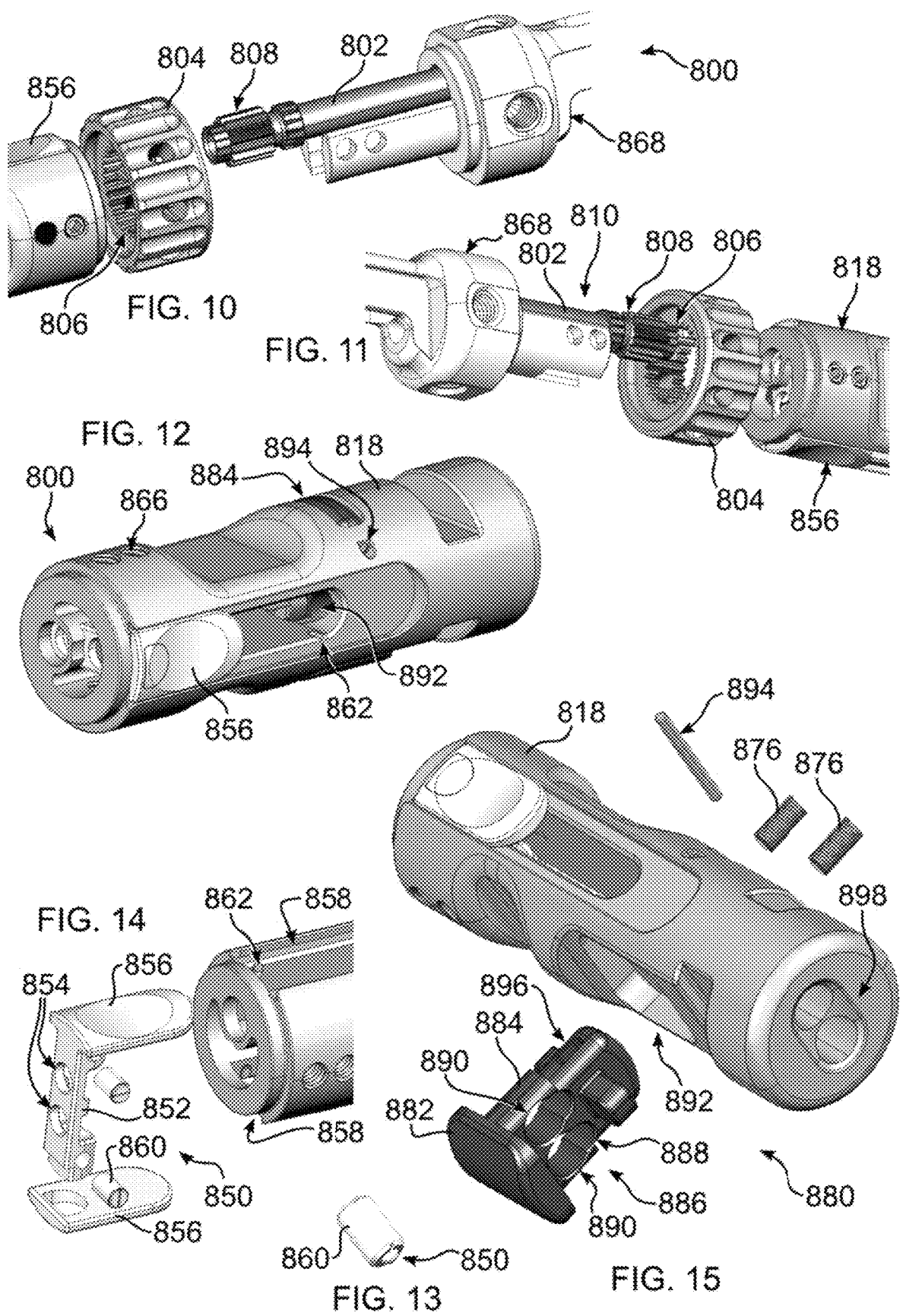

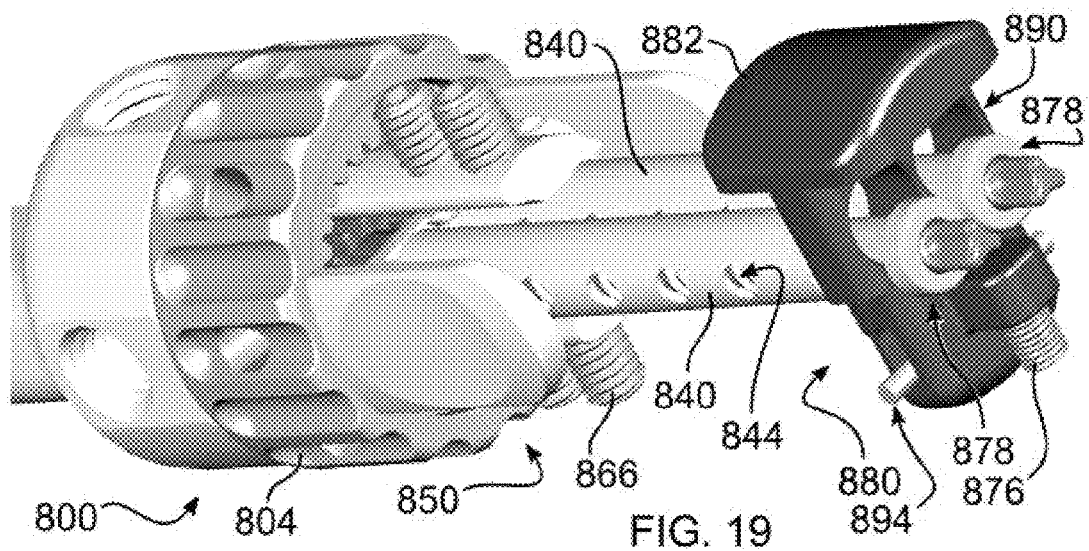
FIG. 19
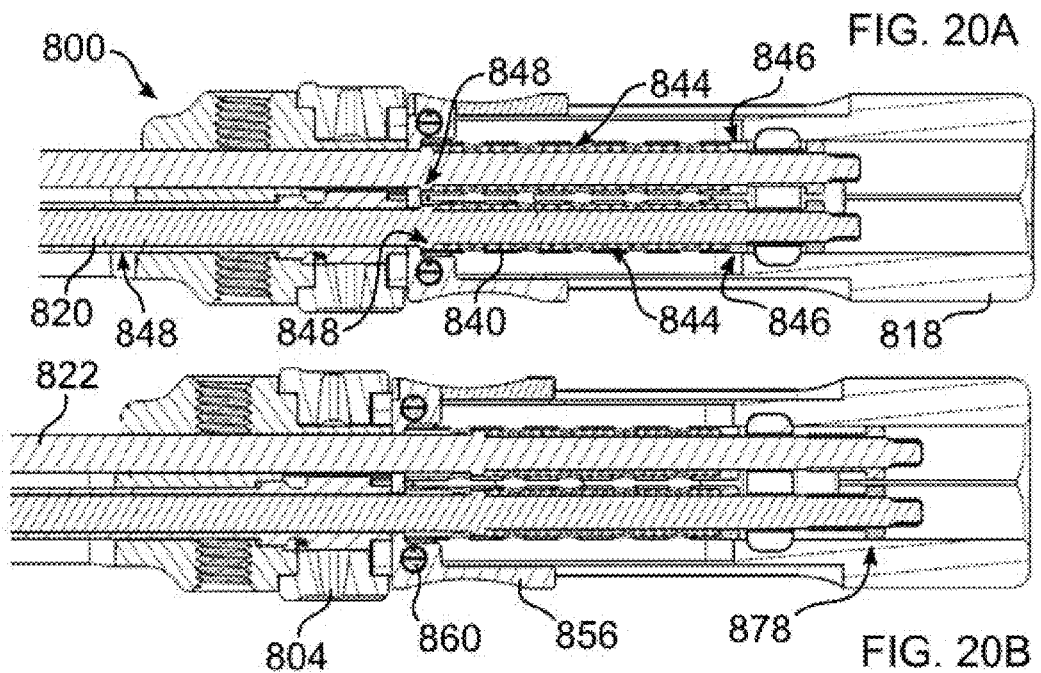
FIG. 20A
FIG. 20B
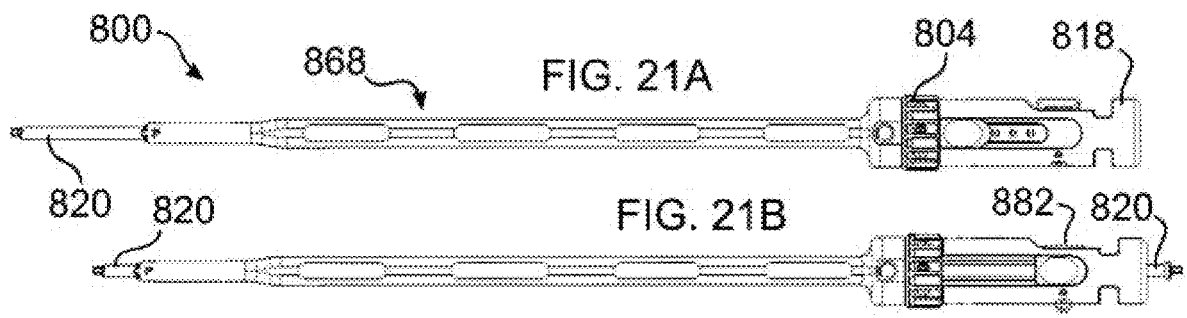
FIG. 21A
FIG. 21B

POSITIONING AND ADJUSTING TWO AXIS JOINT IMPLANTS

CROSS-REFERENCE TO RELATED APPLICATION(S)

The present application is a continuation of U.S. patent application Ser. No. 17/529,371 filed on Nov. 18, 2021, which is a continuation application of U.S. patent application Ser. No. 16/558,364 filed on Sep. 3, 2019 (published as U.S. 2021-0059839) which is hereby incorporated by reference in its entirety for all purposes.

FIELD OF THE DISCLOSURE

The disclosure relates to a system and method for positioning and subsequently adjusting joint implants, and in particular, to inserting and adjusting an implant that is adjustable over two axes.

BACKGROUND OF THE DISCLOSURE

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc may first be partially or fully removed. Typically, an intervertebral fusion device may then be inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with known conventional fusion devices and methodologies. For example, two important factors in intervertebral fusion may be the anterior (lordotic) angle adjustment and posterior height adjustment. The lordotic angle may be important in restoring sagittal balance while the posterior height may aid in restoring disc height and indirect decompression of the neural foramen. While convention fusion devices may allow for in-situ expansion, they do not allow for the lordotic angle and posterior height to be adjusted in-situ independently of one another.

SUMMARY OF THE DISCLOSURE

In an embodiment of the disclosure, a device for inserting and adjusting a therapeutic implant having two rotatable actuators, comprises a body forming a handle portion and having a frame connected to and extending from the handle portion; a tube defining a distal end and an opposed proximal end, having a hollow central bore, supported by the frame to extend away from the body, and having an engagement end at the shaft distal end that is releasably engageable with the implant; first and second stems each having a distal end including a tool end engageable with a rotatable actuator of the implant, having a proximal end rotatable to cause rotation of the distal end to thereby rotate the rotatable actuator of the implant when the tool end is engaged with the implant; the first stem being rotatably and slideably disposed within the hollow central bore of the tube; and the second stem being rotatably and slideably supported by the frame.

In variations thereof, the engagement end at the shaft distal end being a threaded surface mateable with threads of the implant; the tube further includes a peripheral external gear at a proximal end, the device further including a rotatable ring having an internal peripheral gear mateable with the peripheral external gear of the tube, the rotatable ring rotatable to cause rotation of the tube to cause the engagement end of the shaft distal end to engage or disengage with the implant; and/or each of the first and second stems includes a spring bearing upon the body and the stem to urge the stem away from the handle portion of the body and into engagement with the implant when the implant is engaged with the tube.

In further variations thereof, each of the first and second stems has a sleeve concentrically surrounding the stem within the handle portion, the spring concentrically surrounding the stem and inside the sleeve, the sleeve and spring retained within the handle portion by a distal and a proximal block; the first and second stems are releasably engageable from the body by moving at least the proximal block; and/or the spring is retained upon the stem by a stem collar at a distal end of the spring and a flange of the sleeve at a proximal end of the spring, the stem, spring, and collar thereby being mutually connected.

In yet further variations, thereof, the proximal block includes two elongated openings each forming an overlapping small bore and large bore, a sleeve each passable through a large bore and not a small bore, the proximal block movable to align each of either the small bores or the large bores with a sleeve; the distal block slideable within the handle portion to bear upon the sleeve of each stem, and to thereby push the respective sleeve, spring, and stem through the large bore and out of the body when the proximal block is moved to align each of the large bores with a sleeve; and/or the distal block is resiliently mounted within the handle portion to align the small bores with the stems in a resting position, and movable by pressing a button formed at an end of the distal block to a release position in which the large bores are aligned with the stems; and/or each of the stems are independently rotatable.

In other variations, a resiliently mounted cam is associated with one of the distal block and the body and a detent associated with the other of the distal block and the body, the cam and detent releasably engageable as the distal block is moved to define a locked position and a release position; the cam is a ball plunger; the frame includes at least two channels, one of the at least two channels supporting the tube, another of the at least two channels supporting the second stem; the handle portion including two proximal apertures each communicating with a proximal end of a stem; and/or the stems are reversibly removable.

In another embodiment of the disclosure, a device for inserting and adjusting a therapeutic implant having two rotatable actuators, the implant having a threaded connector, where the device comprises a handle; a frame including at least two channels, the frame having a proximal end connected to the handle and a distal end extending away from the handle; a tube defining a distal and an opposed proximal end, having a hollow central bore, supported by the frame to extend away from the body, having threads at the shaft distal end that is releasably engageable with the threaded connector of the implant, and having an external peripheral gear at the proximal end; first and second stems each having a distal end including a tool engagement end engageable with a rotatable actuator of the implant, having a proximal end with a tool engagement rotatable to cause rotation of the distal end to thereby rotate the rotatable actuator of the implant when the tool engagement is engaged with the implant; the first stem being rotatably and slideably disposed within the hollow central bore of the tube, the first stem independently rotatable with respect to the tube; the second stem being rotatably and slideably supported by the frame; and a ring rotatably connected to the handle and including an internal peripheral gear mateable with the external peripheral gear of the tube, the tube thereby rotated by rotation of the ring.

In a variation thereof, each of the first and second stems includes a spring bearing upon the handle and the stem to urge the stem away from the handle portion of the body and into engagement with the implant when the implant is engaged with the tube.

In a further embodiment of the disclosure, a method of inserting and adjusting a therapeutic implant having two rotatable actuators each operable to change a parameter of the implant, comprises connecting the implant to an inserter having: a body forming a handle portion and having a frame connected to and extending from the handle portion; a tube defining a distal end and an opposed proximal end, having a hollow central bore, supported by the frame to extend away from the body, and having an engagement end at the shaft distal end that is releasably engageable with the implant; first and second stems each having a distal end including a tool end engageable with a rotatable actuator of the implant, having a proximal end rotatable to cause rotation of the distal end to thereby rotate the rotatable actuator of the implant when the tool end is engaged with the implant; the first stem being rotatably and slideably disposed within the hollow central bore of the tube; and the second stem being rotatably and slideably supported by the frame; and rotating the first and second stems to change two parameters of the implant.

In a variation thereof, rotating the first and second stems causes a different change in height of two sides of the implant relative to each other, to thereby define a therapeutic lordotic angle.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 1 depicts a perspective side view of an inserter in accordance with the disclosure;

FIG. 2 depicts a perspective top view of an inserter in accordance with the disclosure;

FIG. 3 depicts an end view of an end of the inserter of FIG. 1 which is inserted into the body;

FIG. 4 depicts an end view of an end of the inserter of FIG. 1 which is held;

FIG. 5 depicts a perspective view of an implant insertable and adjustable with the inserter of the disclosure;

FIG. 6 depicts a bottom perspective view of the inserter of FIG. 1, with stems removed;

FIG. 7 depicts a bisected cross-section of an end of the inserter of FIG. 1 and the implant of FIG. 5;

FIG. 8 depicts a top perspective view of the inserter of FIG. 1, with stems removed;

FIG. 9 is a diagram of an implant insertable and adjustable by the inserter of FIG. 1, illustrating a lordotic angle achievable in accordance with the disclosure;

FIG. 10 is an exploded perspective view of a gear configuration of the inserter of FIG. 1;

FIG. 11 is an alternative perspective view of a gear configuration of the inserter of FIG. 1;

FIG. 12 depicts a perspective view of a handle assembly of the inserter of FIG. 1, separated from a frame assembly;

FIG. 13 depicts a perspective view of a plunger ball of the inserter of FIG. 1, as further shown in FIG. 14;

FIG. 14 depicts an exploded view of the handle portion of the inserter of FIG. 1, with a slide assembly removed;

FIG. 15 depicts an exploded view of the handle portion of the inserter of FIG. 1, with a retaining block assembly removed;

FIG. 19 is a perspective view of the handle portion of the inserter of FIG. 1, with the body removed;

FIG. 20A depicts a bisected cross-sectional view of the handle depiction of the inserter of FIG. 1, before engagement of the stems with an implant;

FIG. 20B depicts the inserter of FIG. 20A, after engagement of the stems with an implant;

FIG. 21A depicts a side view of the inserter of FIG. 1 prior to release of stems; and FIG. 21B depicts a side view of the inserter of FIG. 1 after release of stems.

DETAILED DESCRIPTION OF THE DISCLOSURE

Figure 16:
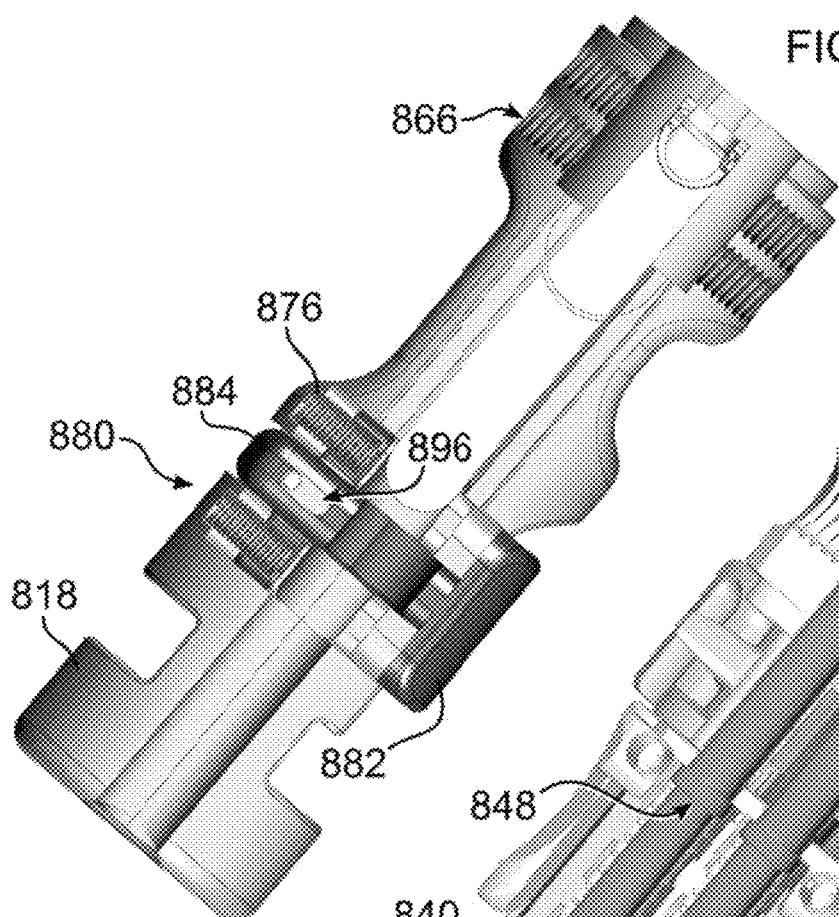
FIG. 16 depicts a bisected cross-sectional view of the handle portion of the inserter of FIG. 1.
Figure 17:
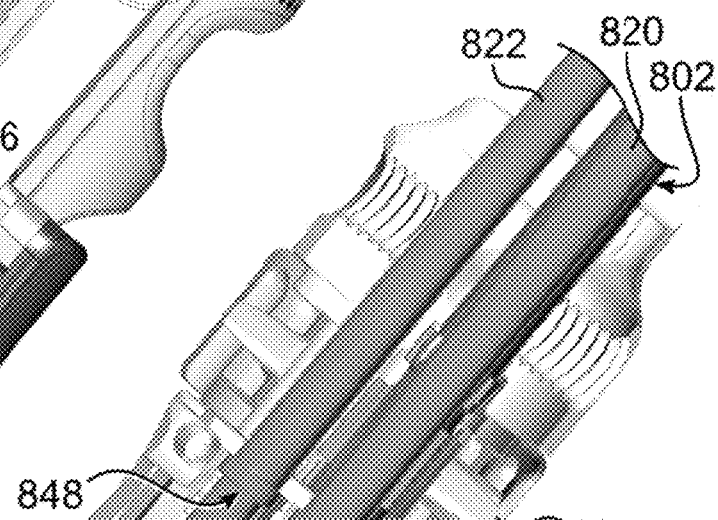
FIG. 17 depicts a bisected cross-sectional view of the handle portion of the inserter of FIG. 1, and a portion of the frame, with the stems in place.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically. Headings are provided for the convenience of the reader and are not to be construed as limiting.

Introduction

A spinal fusion is typically employed to eliminate pain caused by the motion of degenerated disk material. Upon successful fusion, a fusion device becomes permanently fixed within the intervertebral disc space. With reference to FIGS. 5 and 9, an example of an expandable fusion device, or implant 5500 that can be inserted and adjusted in accordance with the disclosure is shown between adjacent vertebral bodies 15 and 20. Implant 5500 may be implanted between two adjacent vertebral bodies 15 and 20 in any section of the spine, including the cervical, thoracic, lumbar, and sacral vertebral sections. More than one expandable fusion device 10 may be implanted within the body, for example, between successive or separated vertebrae. As illustrated, implant 5500 engages the endplates 25 and 30 of the adjacent vertebral bodies 15 and 20 and, in the installed position, maintains normal intervertebral disc spacing and restores spinal stability, thereby facilitating an intervertebral fusion. An implant 5500 can be manufactured from a number of materials including titanium, stainless steel, titanium alloys, non-titanium metallic alloys, polymeric materials, plastics, plastic composites, PEEK, ceramic, and elastic materials.

Two important intervertebral implant parameters for addressing spinal pathologies include lordotic angle and posterior height. The lordotic angle is important, for example, for restoring sagittal balance, while the posterior height aids, at least, in restoring disc height and indirect decompression of the neural foramen. Until the instant disclosure, these parameters could not be adjusted in-situ independently of each other, and particularly without repositioning instruments within the body. In accordance with the disclosure, the medical practitioner can now manipulate both the lordotic angle and height of the implant in situ, without repositioning a tool, to best fit the implant to desired patient anatomy, to thereby more likely obtain a favorable therapeutic result while introducing the least amount of tissue disturbance.

With reference to FIG. 9, expansion of the implant 5500 may be controlled so that the anterior height $H_a$ and the posterior height $H_p$ may be independently controlled. By way of example, the expandable fusion device 10 may have independent anterior expansion and posterior expansion mechanisms, each controlled by a separate actuator, shown here with separate tri-lobe and slotted actuator engagements 5552, 5554, although other engagement types can be employed. By separate control of anterior expansion and posterior expansion, an operator may adjust the expandable fusion device 10 to provide a desired amount of posterior height $H_p$ and lordotic angle $\theta$ (shown in FIG. 9). Alternatively stated, the implant is adjusted along two separate axes. Those of ordinary skill in the art will appreciate that the lordotic angle $\theta$ is dependent on the anterior height $H_a$ and posterior height $H_p$ of implant 5500. In some embodiments, expansion on the anterior side 35 and the posterior side 40 may also be performed simultaneously to maintain a lordotic angle $\theta$ with only changing the anterior height $H_a$ and the posterior height $H_p$ at the same rate.

Implant Engagement

Figure 18:
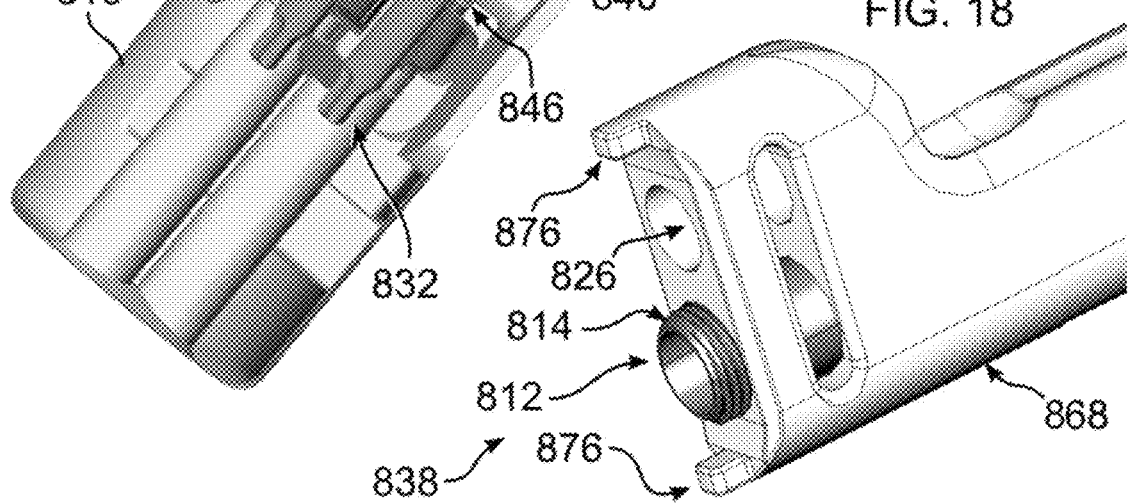
FIG. 18 depicts a perspective view of an inserted end of the inserter of FIG. 1.

The disclosure provides an inserter 800 that reversibly engages/disengages from the implant 5500 (FIGS. 5, 7), or implant 10 (FIG. 9) and which can expand and contract the implant with respect to lordotic angle and height, or any two adjustable parameters of the implant. A cannulated, geared, threaded tube 802 is actuated by an internal ring gear 806 of ring 804 (FIG. 11) for threading and securing the inserter to the implant. The proximal portion 810 of tube 802 has a peripheral gear 808 which matingly engages with an internal ring gear 806 which is concentrically connected to rotatable ring 804 that can be knurled as shown to improve grip by a hand of a user. Rotatable ring 804 is rotatably mounted to a body 818 forming a handle graspable by a user of inserter 800. When rotatable ring 804 is rotated, tube 802 rotates through engagement of gears 806, 808. The distal end 812 of shaft 802 (FIG. 18) has an external thread 814 which is reversibly engaged with mating threads of threaded aperture 635 of implant 5500 (FIG. 5), to securely and reversibly fasten inserter 800 to implant 5500. Tube 802 is rotatably supported by a first channel 824 which can be formed in one or more sections (each marked as 824 in the figures). Alternatives to rotatable ring can include, as examples, directly rotating peripheral gear 808, or other actuator connected to tube 802, for example directly driving an end of tube 802 with a tool engagement.

While distal end 812 is shown with threads 814, other reversible types of engagement are possible, such as a twist-lock or magnetic connection, for example. One or more tabs 876 (FIG. 18) or other mating engagement can additionally be provided at a distal end of frame 868, which engage or mate with a corresponding structure on implant 5500, to provide alignment and additional stability.

Implants 5500 and 10 are described in detail in U.S. Pat. No. 10,052,215, the contents of which is incorporated by reference herein. Herein, implant 5500 is referenced, however it should be understood that the disclosure can be carried out using any implant with two actuators engageable by inserter 800, including implant 10 or other implants of the cited reference, or other known or hereinafter devised implants.

Implant Actuation

A distal end 828 of an elongated stem 820 forming a driver is advanced through the bore of tube 802 to engage with a mating screw 5552 (75 in FIG. 9) or other actuator of implant 5500. A second guide channel 826, which may be formed in one or more sections (each marked as 826 in the figures) enables insertion of a second elongated stem 822, which is engageable at a distal end 830 with a second mating screw 5554 (80 in FIG. 9) or other actuator of implant 5500. Channels 824 and 826 can be supported by a frame 868 that extends from and is unitary with body 818, or is separable as shown in the figures, and is connected to body 818, for example using threaded fasteners 866 (FIG. 19).

A separable driver or other tool (not shown) can be engaged with a proximal end 832 or 834 of stem 820 or 822, each of which is provided with a tool engagement mateable with the separable driver. In the embodiment shown, and as described further elsewhere herein, stem 820 or 822 is pushed further into body 818 when implant 5500 is engaged with implant 5500 (FIG. 20B). The separable driver tool end may be inserted into body 818 to engage stem 820 or 822 when implant 5500 is engaged.

Insertion stems 820, 822 can be provided with any type of driver engagement at distal end 828, 830, respectively, which mates with implant actuators 5552, 5554, and any type of driver engagement at proximal ends 832, 834, with mate with the separable driver, such as hex or torx, or the tri-lobe tips shown.

Stems 820, 822 are rotatable in either direction to each increase or decrease a parameter of implant 5500, such as independently adjusting a height of each side of implant 5500 to affect both an overall height of the implant as well as a lordotic parameter. When a desired amount of adjustment has been made, either or both of stems 820, 822 can be retracted away from the implant, and the tube can be unthreaded from the implant, after which the inserter end may be completely removed from the body.

In accordance with the disclosure, independent control of lordotic angle and posterior height allows the surgeon to better customize the shape and fit of the implant to the patient anatomy. This is unlike known implants where manipulation of both the posterior height and angle is not possible. A tailored fit of both height and angle can help reduce the risk of subsidence and provide an overall better post-surgical result for the patient. The insertion instrument of the disclosure facilitates correct use of variations of implant 5500 which enable such separate control.

With respect to the embodiment of FIGS. 55 et seq. of U.S. Pat. No. 10,052,215 (FIGS. 5 and 7 herein, with FIG. 9 illustrating an alternative implant), and similar implants, in particular, the inserter of the disclosure provides the additional advantage of preventing undesired kyphosis. More particularly, because implant 5500 can be threaded to the inserter via threads at 5534 on the posterior side, inserter 800 can prohibit greater expansion of the posterior side than the anterior side, ensuring implant 5500 is not inserted at a kyphotic angle. As the anterior side of implant 5500 is expanded by rotation of stem 822, the proximal ramp of implant 5500 is drawn toward the distal side of implant 5500. This leave space for the same to occur with the posterior side of implant 5500. However, on the posterior side, as the proximal ramp moves closer to the distal side of the implant, the inserter moves with it because they are firmly attached via threads 814. As the posterior side height is brought to the height of the anterior side, the distal end 838 of inserter 800 is drawn closer to the anterior side of implant 5500 until it abuts on a surface of the proximal side of implant 5500. Accordingly, further expansion of the posterior side is not possible until the anterior side is expanded further.

Positive Stem Engagement

With reference to FIGS. 19-20, in particular, stems 820, 822 are slidably mounted within tube inserter 800 and channels 826, respectively, to enable engagement and disengagement with implant actuators 5552, 5554. Stems 820, 822 each further slide within a sleeve 840 which is disposed within body 818. During use of inserter 800, sleeves 840 are prevented from moving within body 818 by contact with release assemblies 850, 880, which are positioned on opposite ends of each sleeve 840, as explained further elsewhere herein.

Sleeves 840 each house a spring 844. Springs 844 are each confined within a sleeve 840 by a stop flange 846 connected to a proximal end of sleeve 840, and a collar 848 disposed about each of stems 820, 822, each stem axially disposed within a sleeve 840 and a spring 844. As a result, as stems 820, 822 are moved axially by contact with implant 5500 through a sleeve 840, spring 844 is compressed, urging stem 820 or 822 in a counter direction towards implant 5500, for example from the position of FIG. 20A to the position of FIG. 20B. Accordingly, distal ends 820 and 830 are maintained within mating engagement with actuators 5552, 5554 of implant 5500 as implant 5500 is manipulated into position and subsequently adjusted. In addition, stop flange 846 and collar 848 engage the stem with the sleeve 840 and spring 844.

In addition to providing a positive engagement between stems 820, 822 and implant 5500, springs 844 enable a given set of stems 820, 822 to work with implants of differing configurations. For example, actuators 5552, 5554 may be positioned closer or farther from the threaded engagement formed between external thread 814 and threaded aperture 635 of implant 5500. Springs 844 enable stems 820, 822 to axially advance as needed to engage actuators 5552, 5554, while maintaining the same positive engagement regardless of such distance. Springs 844 are selected to provide a desired engagement force throughout a range of contact distances anticipated.

Stem Removal/Replacement

The disclosure provides for replacing stems 820, 822, for example to include longer or shorter stems, or stems with different end engagements, and to clean the stems and associated components. With reference in particular to FIGS. 12-17, 19, and 21, two release assemblies, slide release assembly 850 and stop release assembly 880, cooperate to retain stems 820, 822, sleeves 840, and springs 844, within inserter 800.

Stop release assembly 880 includes a stop button 882 accessible on an external surface of body 818. A blocking surface 884 extends from stop button 882, and includes two elongated aperture 886 each having an overlapping large bore 888 and small bore 890. When stop button 882 is pressed, blocking surface 884 slides in a slot 892 within body 818, moving along an axis transverse to a longitudinal axis of inserter 800. A pin 894 passes through body 818 and resides within an elongated channel 896 within blocking surface 884. In this manner, an extent of movement of blocking surface 884 is limited by the dimensions of elongated channel 896 and pin 894.

One or more springs 898 bear against body 818 and blocking surface 884 to thereby urge stop button 882 and blocking surface 884 in an outward, locking direction, whereby stems 820, 822 each pass through a small bore 890 portion of an elongated aperture 886. Small bore 890 is sized so that a sleeve 840 cannot pass therethrough. In this manner, stems 820, 822 are retained within body 818. Additionally, stem 820 or 822 cannot pass through spring 844 and sleeve 840 as they are collectively mutually engaged by collar 848 and flange 846, requiring that these components must pass through large bore 888 together in order to pass outside of body 818.

To remove stems 820, 822, from a secured position stop button 882 is pressed, causing stems 820, 822 to pass from the small bores 890 into the large bores 888, the latter having a diameter larger than the sleeves 840. Stems 820, 822 are now free to emerge from a proximal end 898 of body 818 (FIG. 21B). To urge stems 820, 822 towards proximal end 898, slide release assembly 850 is deployed.

More particularly, slide release assembly 850 includes a slide block 852 having two apertures 854 each sized to allow a stem 820 or 822 to pass, but sized smaller than sleeve 840. Slide block 852 is connected to at least one slide button 856 each accessible at a surface of body 818. Slide block 852 passes through at least one slot 858 opening from an interior of body 818 to an exterior of body 818. extends between two slide buttons 856. In the embodiment shown in the figures, there are two slide buttons 856 and two slots 858 on opposing sides of body 818. As such, slide button 856 may be moved to cause slide block 852 to bear upon sleeves 840 to push sleeves 840 together with springs 844 and stems 820, 822 through large bores 888 and out of body 818.

To further control movement of slide block 852, a detent and detent follower can be formed between slide release assembly 850 and body 818. As shown in FIGS. 13-14, one or more ball plungers 860 (a spring loaded roller ball) is mounted to slide block 852 or slide buttons 856, and one or mating detents 862 (FIGS. 12 and 14) is formed in body 818 for each ball plunger 860. Detents 862 can be placed at a location corresponding to stem securing or locking position of slide block 852 (FIG. 14) and a stem releasing position of slide block 852 (FIG. 12). Slots 858 can be dimensioned so that the ball 864 of ball plunger 860 bears upon a surface throughout a length of travel of ball plunger 860, to guide and further secure slide block 852.

It should be understood that ball plungers 860 can alternatively be mounted upon body 818, and detents 862 can be positioned upon slide block 852 or slide buttons 856. Other detent following cam structures can be provided, for example a resilient tab (not shown) in place of ball plunger 860.

Bushings 878 can be provided at a proximal end of each of stems 820, 822, sized to correspond with small bore 890 and fabricated of a material, such as a polymer, which promotes smooth passage of stems 820, 822 through small bore 890.

In an embodiment, implant 5500 together with an inserted portion of inserter 800 of the disclosure can be configured to be placed into the body through an endoscopic tube or cannula. Inserter 800 of the disclosure can be used to implant other types of devices into the body, to be positioned within other joints of the body or elsewhere in the body, particularly where two parameters of the implanted device must be adjusted.

Inserter 800 can be fabricated using any biocompatible materials of sufficient strength and durability. If inserter 800 is to be reused, it can be made with materials that can withstand the intended method of sterilization. Examples include one or more of titanium, stainless steel, titanium alloys, non-titanium metallic alloys, polymeric materials, plastics, plastic composites, PEEK, ceramic, and elastomeric materials.

The components of the systems and apparatuses may be integrated or separated. Moreover. The systems and apparatuses disclosed herein may be performed by more, fewer, or other components, and methods may include more, fewer, or other steps. Applicants do not intend any of the claims to invoke 35 U.S.C. 112(f) unless the words "means for" or "step for" are explicitly used in the particular claim.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A method for inserting and adjusting an intervertebral implant having two rotatable actuators, comprising the steps of:
   providing the intervertebral implant having two rotatable actuators;
   providing an instrument having:
   a body with a handle portion having a rotatable ring with an internal gear and an elongated frame extending from the handle portion;
   a tube supported by the frame and extending away from the body, the tube having a distal end configured to threadably engage the implant, a proximal end comprising an external gear, and a hollow central bore therethrough;
   a first stem slidably disposed in the hollow central bore of the tube; and
   a second stem supported by the frame;
   wherein the internal gear of the rotatable ring is configured to engage the external gear of the tube such that rotation of the rotatable ring causes rotation of the tube to facilitate engaging or disengaging the distal end of the tube with the implant;
   wherein the first stem and the second stem each have a distal tool end configured to be inserted into the implant to engage with a respective one of the two rotatable actuators of the implant and a proximal end rotatable to cause rotation of the respective distal tool end to thereby rotate the respective rotatable actuator of the implant;
   wherein the first stem is configured to rotate to adjust the implant along a first axis, and wherein the second stem is configured to rotate to adjust the implant along a second axis; and
   positioning the implant with the instrument between adjacent vertebral bodies.

2. The method of claim 1, the distal end of the tube being a threaded surface mateable with threads of the implant.

3. The method of claim 1, the tube further including a peripheral external gear at the proximal end, the rotatable ring having an internal peripheral gear mateable with the peripheral external gear of the tube.

4. The method of claim 1, each of the first and second stems including a spring bearing upon the body and the respective stem to urge each stem away from the body and into engagement with the implant when the implant is engaged with the tube.

5. The method of claim 4, each of the first and second stems having a sleeve concentrically surrounding the respective stem within the handle portion, each spring concentrically surrounding the respective stem and arranged inside the respective sleeve, and each sleeve and respective spring retained within the handle portion by a distal block and a proximal block.

6. The method of claim 5, each of the first and second stems releasably engageable from the body by moving at least the proximal block.

7. The method of claim 6, wherein each spring is retained upon each respective stem by a stem collar at a distal end of the respective stem and a flange of the respective sleeve at a proximal end of the sleeve, such that each respective stem, spring, and collar are thereby mutually connected.

8. The method of claim 5, the proximal block including two elongated openings each having an overlapping small bore and large bore, each sleeve passable through a respective one of the large bores and not passable through the respective overlapping small bore, the proximal block movable to align each of either the small bores or the large bores with one of the sleeves.

9. The method of claim 8, the distal block slideable within the handle portion to bear upon the sleeve of each of the first and second stems, and to thereby push the respective sleeve, spring, and stem through the respective large bore and out of the body when the proximal block is moved to align each of the large bores with one of the sleeves.

10. The method of claim 8, the distal block resiliently mounted within the handle portion to respectively align the small bores with the first and second stems in a resting position, and movable by pressing a button formed at an end of the distal block to a release position in which the large bores are respectively aligned with the first and second stems.

11. The method of claim 1, wherein each of the first and second stems are independently rotatable.

12. The method of claim 9, further comprising a resiliently mounted cam associated with one of the distal block and the body and a detent associated with the other of the distal block and the body, the cam and the detent releaseably engageable as the distal block is moved to define a locked position and a release position.

13. The method of claim 12, wherein the cam is a ball plunger.

14. The method of claim 1, the frame including at least two channels, one of the at least two channels supporting the tube, and another of the at least two channels supporting the second stem.

15. The method of claim 1, the handle portion including two proximal apertures each communicating with a proximal end of one of the first and second stems.

16. The method of claim 1, the first and second stems being reversibly removable.

17. A method of inserting and adjusting a therapeutic implant having two rotatable actuators each operable to change a parameter of the implant, comprising:
connecting the implant to an inserter having:
a body forming a handle portion and having a frame connected to and extending from the handle portion;
a tube:
defining a distal end and an opposed proximal end,
having a hollow central bore,
supported by the frame to extend away from the body, and
having an engagement end at the distal end that is releasably engageable with the implant;
first and second stems each:
having a distal end including a tool end engageable with a rotatable actuator of the implant, and
having a proximal end rotatable to cause rotation of the distal end to thereby rotate the rotatable actuator of the implant when the tool end is engaged with the implant;
the first stem being rotatably and slideably disposed within the hollow central bore of the tube; and
the second stem being rotatably and slideably supported by the frame;
positioning the implant with the inserter between adjacent vertebral bodies; and
rotating the first and second stems to change two parameters of the implant.

18. The method of claim 17, wherein rotating the first and second stems causes a different change in height of two sides of the implant relative to each other, to thereby define a therapeutic lordotic angle.

* * * * *